United States Patent [19]

Degwert et al.

[11] Patent Number: 5,708,028
[45] Date of Patent: Jan. 13, 1998

[54] USE OF CIS-9-HEPTADECENOIC ACID FOR TREATING PSORIASIS AND ALLERGIES

[75] Inventors: Joachim Degwert, Tostedt; Jurgen Jacob; Friedhelm Steckel, both of Hamburg, all of Germany

[73] Assignee: Beiersdorf AG, Hamburg, Germany

[21] Appl. No.: 525,594

[22] PCT Filed: Mar. 24, 1994

[86] PCT No.: PCT/EP94/00941

§ 371 Date: Sep. 20, 1995

§ 102(e) Date: Sep. 20, 1995

[87] PCT Pub. No.: WO94/21247

PCT Pub. Date: Sep. 29, 1994

[30] Foreign Application Priority Data

Mar. 25, 1993 [DE] Germany .................. 43 09 512.7

[51] Int. Cl.$^6$ ................................................ A61K 31/20
[52] U.S. Cl. ................................... 514/560; 514/863
[58] Field of Search ............................. 514/560, 863

[56] References Cited

FOREIGN PATENT DOCUMENTS 9215292  9/1992  WIPO .

OTHER PUBLICATIONS

HCAPLUS Abstract 1993: 66867, Martin (1992).

Primary Examiner—Marianne M. Cintins
Assistant Examiner—M. Moezie
Attorney, Agent, or Firm—Sprung Kramer Schaefer & Briscoe

[57] ABSTRACT

Cis-9-heptadecenoic acid or its salts can be used for the prophylaxis and treatment of psoriasis, allergies and autoimmune diseases.

2 Claims, No Drawings

USE OF CIS-9-HEPTADECENOIC ACID FOR TREATING PSORIASIS AND ALLERGIES

DESCRIPTION

This application is a 371 of PCT/EP94/00941 Mar. 24, 1994.

The invention relates to new uses of cis-9-heptadecenoic acid.

Saturated and unsaturated fatty acids are constituents of the cell membrane of cells. The concentration of unsaturated fatty acids plays a role in the barrier properties of the skin and in the reactivity of calls in inflammatory processes.

An anti-inflammatory and oedema-inhibiting action has been described for the monounsaturated fatty acid cis-9-heptadecenoic acid in German Auslegeschriften 1 195 296 and 1 147 221. It is said to have an activity in cases of acute and chronic dermatitis, in particular on burn wounds and in the treatment of "Ulcera cruris". A reduction of an induced granuloma tissue in the rat under the influence of cis-9-heptadecenoic acid and an inactivity of oleic acid in this test set-up has been reported. This is in contrast to the findings of Gor'kova et al. (Chemical Abstracts Vol. 68, (1968) 1909 u), who found an activity of oleic acid and an increased cellular infiltrate in an induced granuloma in the rat under the influence of cis-9-heptadecenoic acid.

Surprisingly, it has now been found that cis-9-hepta-1-decenoic acid is active on psoriasis, allergies and autoimmune diseases.

The invention relates to the use of cis-9-heptadecenoic acid and/or its salts for the prophylaxis and treatment of psoriasis, allergies and autoimmune diseases.

cis-9-Heptadecenoic acid is known and is obtainable by known processes or by isolation from animal tissue. Physiologically tolerated salts of cis-9-heptadecenoic acid are preferred.

The term psoriasis means this skin disease in all its manifestations.

Allergies are, in particular, atopy and contact allergies. Atopy manifests itself, for example, as allergic conjunctivitis, allergic rhinitis, allergic asthma or neurodermatitis.

Autoimmune diseases are, in particular, the diseases of the rheumatic type.

Surprisingly, the active compounds according to the invention are active against diseases which are so different in principle, such as psoriasis, allergies and autoimmune diseases.

For prophylaxis, the active compounds are administered to lessen the incidence and intensity of manifestations of the diseases. Treatment in the manifest stage leads to shortening thereof and to alleviation of the symptoms. cis-9-Heptadecenoic acid can suppress or reduce the release of important triggering mediators, such as $TNF\alpha$.

Water-soluble salts of cis-9-heptadecenoic acid, in particular the alkali metal salts, for example the sodium salt or the potassium salt, and also the ammonium salt, are preferred. The calcium, magnesium and aluminium salt and also the salts of organic bases, for example amines, such as ethanolamine, ethylenediamine and morpholine, are also suitable.

Pharmaceutical preparations, agents or compositions which comprise the compound according to the invention or a pharmaceutically acceptable salt thereof together with a pharmaceutically acceptable diluent or carrier are also provided according to the invention.

The compounds of the present invention can be used on humans orally or parenterally, for example in a dosage of 0.05 to 500 mg, preferably 0.5 to 50 mg, particularly preferably 0.1 to 10 mg per day, and in particular also in subdivided doses, for example two to four times daily.

The compounds according to the invention can also be incorporated without problems into customary pharmaceutical and cosmetic bases for topical applications, and the corresponding topical pharmaceutical and cosmetic formulations or compositions are thus obtained. They are preferably employed in amounts of 0.001 to 10% by weight, in particular in amounts of 0.01 to 1% by weight, in each case based on the total weight of the topical composition. The formulations can be used several times daily in the customary manner.

The invention also relates to the use of the active compounds according to the invention for the preparation of pharmaceutical compositions and topical pharmaceutical and cosmetic compositions for the prophylaxis and treatment of psoriasis, allergies and autoimmune diseases.

The invention likewise also relates to the use of pharmaceutical compositions and topical pharmaceutical and cosmetic compositions having a content of cis-9-heptadecenoic acid and/or its salts for the prophylaxis and treatment of psoriasis, allergies and autoimmune diseases.

Surprisingly, it has been found that in the lymphocyte transformation test, cis-9-heptadecenoic acid inhibits the activation of lymphocytes and thus influences processes in which lymphocytes participate, for example in the case of allergies, psoriasis and autoimmune diseases.

cis-9-Heptadecenoic acid showed both a certain inflammatory macrophage-stimulating potency and an anti-inflammatory macrophage-stimulating potency in the macrophage differentiation test. In processes which are characterized by a certain absence of acutely inflammatory macrophages, for example psoriasis, the substance thus has the ability to induce these and therefore to normalize the inflammatory process. This applies in particular because of the ability, which has further surprisingly been found, to reduce the production of $TNF\alpha$ by macrophages to a stimulus. The reactivity of cells to react to a stimulus is thereby reduced and the reaction threshold increased. This is of importance in the prophylaxis of cytokinin-induced processes, such as, for example, psoriasis, atopy, allergies or autoimmune diseases.

The above results are presented in an attached test report.

The active compounds according to the invention can be mixed with customary pharmaceutically acceptable diluents or carriers and if appropriate with other auxiliaries and administered, for example, orally or parenterally. They can preferably be administered orally in the form of granules, capsules, pills, tablets, film-coated tablets, lacquered tablets, syrups, emulsions, suspensions, dispersions, aerosols and solutions, as well as liquids, or also as suppositories, vaginal beads or parenterally, for example in the form of solutions, emulsions or suspensions. Preparations for oral administration can comprise one or more additives, such as sweeteners, flavouring agents, dyestuffs and preservatives. Tablets can comprise the active compound mixed with customary pharmaceutically acceptable auxiliaries, for example inert diluents, such as calcium carbonate, sodium carbonate, lactose and talc, granulating agents and agents which promote the disintegration of tablets after oral administration, such as starch or alginic acid, binders, such as starch or gelatin, and lubricants, such as magnesium stearate, stearic acid and talc.

Suitable carriers are, for example, lactose, gelatin, maize starch, stearic acid, ethanol, propylene glycol, ethers of tetrahydrofurfuryl alcohol and water.

The formulations are prepared, for example, by extending the active compounds with solvents and/or carriers, if appropriate using emulsifying agents and/or dispersing agents, and, for example, in the case of the use of water as a diluent, organic solvents can be used as auxiliary solvents if appropriate.

The formulations are administered in the customary manner, preferably orally or parenterally, in particular perlingually or intravenously. In the case of oral use, tablets can of course also comprise, in addition to the carriers mentioned, additives, such as sodium citrate, calcium carbonate and dicalcium phosphate, together with various adjuvants, such as starch, preferably potato starch, gelatin and the like. Lubricants, such as magnesium stearate, sodium laurylsulphate and talc, can furthermore be co-used for tablet-making. In the case of aqueous suspensions and/or elixirs intended for oral uses, various flavour-improving agents or dyestuffs, in addition to the abovementioned auxiliaries, can be added to the active compounds.

In the case of parenteral use, solutions of the active compounds can be employed, using suitable liquid carrier materials.

Capsules can comprise the active compound as the only constituent or as a mixture with a solid diluent, such as calcium carbonate, calcium phosphate or kaolin. Injectable preparations are likewise formulated in a manner known per se.

The pharmaceutical preparations can comprise the active compound in an amount of 0.1 to 90 per cent by weight, in particular 1–90 % by weight. Capsules are particularly preferred. Individual doses preferably comprise the active compounds in an amount of 1 to 10 mg.

If salts are sparingly soluble in water, they can be administered in the form of suspensions. The sodium and the potassium salts of cis-9-heptadecenoic acid have a particularly good solubility in water. For example, salts are preferably injected intravenously or intramuscularly in the form of an aqueous solution, such as physiological saline solution. The ampoules contain, for example, 2.5 mg of the fatty acid salt per 5 ml of solution. Ampoules with, for example, 45 mg of fatty acid salt per milliliter of solution can also be prepared.

The topical compositions according to the invention can be formulated as liquid, pasty or solid formulations, for example as aqueous or alcoholic solutions, aqueous suspensions, emulsions, ointments, creams, oils, powders or sticks. Depending on the desired formulation, the active compounds can be incorporated into pharmaceutical and cosmetic bases for topical applications which comprise, as further components, for example, oily components, fat and waxes, emulsifiers, anionic, cationic, ampholytic, zwitterionic and/or nonionic surfactants, lower mono- and polyhydric alcohols, water, preservatives, buffer substances, thickeners, fragrances, dyestuffs and clouding agents. Emulsions, for example W/O emulsions, or ointments are preferably used.

It is furthermore preferable according to the invention to add antioxidants to the active compounds and the pharmaceutical and topical compositions. The use of naturally occurring compounds or compounds identical to those in nature, such as, for example, tocopherols, is particularly preferred here. The compositions according to the invention comprise the antioxidants mentioned, for example, in amounts of 0.01–5% by weight, in particular 0.5–2% by weight, based on the entire composition. They are used for stabilizing the active compound.

In the context of the present Application, unless stated otherwise, amounts and percentage data are based on the weight and the total composition of the formulation.

EXAMPLE 1

| Cream: | Parts by weight |
|---|---|
| Polyoxyethylene (20) sorbitan monostearate (polysorbate 60) | 5 |
| Cetylstearyl alcohol | 10 |
| Glycerol 85% | 10 |
| White vaseline | 25 |
| α-D-Tocopherol | 1 |
| cis-9-Heptadecenoic acid Na salt | 1 |
| Optionally dyestuffs, fragrances, water | to 100 |

The cream is prepared in a manner known per se. The oily phase and the aqueous phase are prepared separately by mixing the constituents, if appropriate with gentle heating. The phases are then mixed and emulsified.

EXAMPLE 2

| Cream: | Parts by weight |
|---|---|
| Polyoxyethylene (20) sorbitan monostearate (polysorbate 60) | 5 |
| Cetylstearyl alcohol | 10 |
| Glycerol 85% | 10 |
| White vaseline | 25 |
| α-D-Tocopherol | 1 |
| cis-9-Heptadecenoic acid | 0.1 |
| Optionally dyestuffs fragrances, water | to 100 |

The cream is prepared in a manner known per se. The oily phase and the aqueous phase are prepared separately by mixing the constituents, if appropriate with gentle heating. The phases are then mixed and emulsified.

Preparation of Tablets and Capsules

Tablets and capsules which contain the constituents listed below are prepared by known procedures. These are suitable for treatment of the abovementioned diseases in dosage amounts of in each case one tablet or capsule once or several times daily.

EXAMPLE 3

| Constituents | Weight (mg) Tablet | Weight (mg) Capsule |
|---|---|---|
| cis-9-Heptadecenoic acid | 5 | 10 |
| Tragacanth | 10 | |
| Lactose maize starch | 247.5 | |
| Maize starch | 25 | |
| Talc | 15 | |
| Magnesium stearate | 2.5 | |
| Ascorbic acid | 1 | 0.1 |

EXAMPLE 4

| Constituents | Weight (mg) | |
|---|---|---|
| | Tablet | Capsule |
| cis-9-Heptadecenoic acid Na salt | 10 | 5 |
| Tragacanth | 10 | |
| Lactose maize starch | 247.5 | |
| Maize starch | 25 | |
| Talc | 15 | |
| Magnesium stearate | 2.5 | |
| Ascorbic acid | 1 | 0.1 |

Preparation of Ampoules

Ampoules which contain the constituents mentioned below can be prepared in a known manner. The active compound is dissolved in water and glass ampoules are filled with the solution under nitrogen.

EXAMPLE 5

| cis-9-Heptadecenoic acid Na salt | 5 mg |
|---|---|
| Distilled water to | 5 ml |

EXAMPLE 6

| cis-9-Heptadecenoic acid Na salt | 2.5 mg |
|---|---|
| Distilled water to | 2 ml |

Test Results a) Lymphocyte transformation test according to Al-Tawil et al.

cis-9-Heptadecenoic acid was investigated in the lymphocyte transformation test in various concentrations (0.00156–0.0125% by weight). The substance showed significant inhibition of mitogen-induced proliferation of lymphocytes and therefore has an anti-inflammatory immunomodulating potency.

TABLE 1

| Concentration of cis-9-heptadecenoic acid in the LTT test in % by weight | Inhibition of lymphocyte activation in % |
|---|---|
| 0.01250 | 100 |
| 0.00625 | 90 |
| 0.00312 | 20 |
| 0.00156 | 5 | b) Influence of cis-9-heptadecenoic acid on macrophage differentiation

Human monocytes were isolated from heparinized blood of healthy donors by density gradient centrifugation and were cultured in 96-well tissue culture plates at $5 \times 10^4$ cells/well in McCoy's medium with 10% human AB serum. Concentrations of 0.01 to 0.00001% by weight cis-9-heptadecenoic acid were added to the cells and the cells were incubated at 37° C. (7% of $CO_2$) for 96 hours. The cells were then fixed and the expression of differentiation antigens was measured by indirect immunoperoxidase staining with the aid of monoclonal antibodies. The increased expression of one antigen (acute marker), characterized by the monoclonal antibody 27E10, is typical of acutely inflammatory macrophages, and the increased expression of another antigen (moderate marker), characterized by the monoclonal antibody RM 3/1, is typical of macrophages in the healing phase of inflammations.

cis-9-Heptadecenoic acid stimulates both the acute and the moderate marker. In chronic processes, the active compound can break through the halted progress by a certain renewed activation and induce healing. Stimulation of the moderate marker indicates the potency of having an anti-inflammatory action in acute inflammatory processes.

TABLE 2

| Concentration of cis-9-heptadecenoic acid in % by weight in the medium | Increase in the expression of differentiation antigens on macrophages compared with the control | |
|---|---|---|
| | Acute marker | Moderate marker |
| 0.01 | − | 0 |
| 0.001 | + | + |
| 0.0001 | ++ | + |
| 0.00001 | ++ | ++ |

−: reduction
0: as control
+: slight increase
++: significant increase c) Lipopolysaccharide-induced release of TNFα by human macrophages Human monocytes were isolated from heparinized blood of healthy donors by density gradient centrifugation and were cultured in 96-well tissue culture plates at $5 \times 10^4$ cells/well in McCoy's medium with 10% human AB serum. 30 minutes before stimulation of the cultured cells by 0.0001 to 0.1 µg/ml of lipopolysaccharide (LPS) from S. minnesota (Sigma order No. 7645), 0.001% by weight of active compound was added to the cells. After 96 hours, the supernatants were removed from the cells and the TNFα content therein was determined with the aid of an Elisa test (Genzyme).

cis-9-Heptadecenoic acid significantly reduces the TNFα concentration in the cell supernatants (Table 3).

TABLE 3

| µg/ml of LPS | % reduction in the TNFα concentration in the supernatant by 0.001% of cis-9-heptadecenoic acid |
|---|---|
| 0.1 | 21 |
| 0.01 | 19 |
| 0.001 | 83 |
| 0.0001 | 100 |

We claim:

1. A method of treating psoriasis and allergies which comprises administering to a patient in need thereof an effective amount of a composition consisting essentially of cis-9-heptadecenoic acid or a salt thereof, a pharmaceutically acceptable carrier and optionally an antioxidant.

2. The method according to claim 1, wherein the treatment is for control of psoriasis or atopy.

* * * * *